US00PP08882P

United States Patent [19]

van Andel

[11] Patent Number: Plant 8,882

[45] Date of Patent: Sep. 6, 1994

[54] MINI-SPRAY CARNATION PLANT NAMED 'STAGIROS'

[75] Inventor: Jacob van Andel, Aalsmeer, Netherlands

[73] Assignee: Van Staaveren, B.V., Aalsmeer, Netherlands

[21] Appl. No.: 99,780

[22] Filed: Jul. 29, 1993

Related U.S. Application Data

[63] Continuation of Ser. No. 770,402, Oct. 3, 1991, abandoned.

[51] Int. Cl.[5] ..... H01H 5/00

[52] U.S. Cl. ..... Plt./70.2

[58] Field of Search ..... Plt. 70.1, 70.2, 70.6, Plt. 70.5

[56] References Cited

U.S. PATENT DOCUMENTS

PLT7849 3/1992 van Andel ..... PLT/70.2

*Primary Examiner*—Howard J. Locker

*Attorney, Agent, or Firm*—Tilton, Fallon, Lungmus & Chestnut

[57] ABSTRACT

A new and original variety of mini-spray carnation particularly distinguished by its many bright cyclamen purple flat blossoms of relatively small size, which are borne profusely and intermittently in clusters on erect stems branching from the main stem of an upright bush that has a height of about 100 cm.

1 Drawing Sheet

This application is a continuation application Ser. No. 07/770,402 filed Oct. 3, 1991 abandoned.

This new carnation plant originated as a sport of the variety Statropur (U.S. Plant Pat. No. 7,849) being grown at our nursery in Aalsmeer, Holland. This particular sport was discovered by me and attracted my attention because of its profuse production of unusual cyclamen purple colored flowers and the overall high quality of the plant growth habit. This plant is a sport of unknown causation. The sport was found as a branch of Statropur. Stagiros differs from the parental cultivar in its overall plant height, the color of its petals, and its fruit fertility. Listed below in Table 1 is a comparison of Stagiros with Statropur and other known sports of Statropur. The other sports provided in Table 1 are subjects of copending applications. Serial numbers for these applications are provided in the Table.

TABLE 1

| | STAGIROS | STATROPUR |
|---|---|---|
| SERIAL NO.: | 08/099,780 | 07/611,504 |
| RELATED APPLICATIONS: | 08/099,780 is a Continuation of 07/770,402 (Abandoned) | — |
| PATENT NO.: | — | U.S. Plant Pat. No. 7,849 |
| PETAL BODY: | RHS 73-A + RHS 73-D ("Mottled Portion") | RHS 74-B |
| PETAL BASE: | RHS 155-D | White |
| REVERSE SIDE: | RHS 73-D | White |
| STIGMA: | RHS 155-D | White |
| STYLE: | RHS 155-D | White |
| HEIGHT: | 100 cm. (average) | 150 cm. (average) |
| DISCOLORATION AFTER FULL BLOOM: | Slight | None |
| FERTILE FRUIT: | No | Yes |

| | STAGILAC | STAVIOLET |
|---|---|---|
| SERIAL NO.: | 08/099,271 | 08/098,842 |
| RELATED APPLICATIONS: | 08/099,271 is a Continuation of 07/756,798 (Abandoned) | 08/098,842 is a Continuation of 07/770,403 (Abandoned) |
| PATENT NO.: | — | — |
| PETAL BODY: | RHS 74-A | RHS 74-A |

TABLE 1-continued

| | | |
|---|---|---|
| PETAL BASE: | RHS 155-D | RHS 155-D |
| REVERSE SIDE: | RHS 72-C | RHS 155-D |
| STIGMA: | RHS 155-D | RHS 155-D |
| STYLE: | RHS 155-D | RHS 155-D |
| HEIGHT: | 100–110 cm. (average) | 100–100 cm. (average) |
| DISCOLORATION AFTER FULL BLOOM: | Slight | Slight |
| FERTILE FRUIT: | No | No |

| | STAGIBORD |
|---|---|
| SERIAL NO.: | 08/100,073 |
| RELATED APPLICATIONS: | 08/100,073 is a Continuation of 07/770,401 (Abandoned) |
| PATENT NO.: | — |
| PETAL BODY: | RHS 57-B + RHS 57-A ("Mottled Portion") |
| PETAL BASE: | RHS 155-D |
| REVERSE SIDE: | RHS 62-D |
| STIGMA: | RHS 64-B |
| STYLE: | RHS 64-B |
| HEIGHT: | 100–120 cm. (average) |
| DISCOLORATION AFTER FULL BLOOM: | Slight |
| FERTILE FRUIT: | No |

Asexual propagation of this plant was done by means of cuttings under my direction at Aalsmeer; and propagation of this new plant was continued through successive generations to determine whether the novel characteristics of this plant would be retained from generation to generation and whether its homogeneity could be assured. This proved to be successful and this new carnation variety is now being propagated at Aalsmeer.

DESCRIPTION OF THE DRAWING

My new carnation cultivar is illustrated by the accompanying photographic drawing which, in full color, shows blooming stems with buds and flowers in several stages of development, the color rendition being as nearly true to that herein specified as is reasonably possible to obtain by professional photographic procedures.

DESCRIPTION OF THE NEW PLANT

The following is a detailed description of my new carnation variety based upon observation of plants grown in greenhouse as well as outdoors at Aalsmeer and blooming during the current year. The color designations stated herein are according to the R.H.S. Colour Chart published by The Royal Horticultural Society of London, England.

THE PLANT

Origin: Sport.
Parentage:
*Statropur.*—U.S. Plant Pat. No. 7,849.
Classification:
*Botanic.*—Dianthus hybrid.
*Commercial.*—Mini-spray carnation.
Form: Strong, upright bush.
Height: 100 cm. in average.
Main stem:
*Length.*—In average about 80 cm.
*Growth.*—Strong and upright and fast.
*Branching character.*—The main stem has 7–8 side branches and each side branch has 2–3 branches and each of these branches has 1–2 branches.
Foliage:
*Quantity.*—Medium.
*Number of leaves.*—22–26.
Leaf:
*Size.*—Length: 7–11 cm. Width: 1–2 cm.
*Shape.*—Elliptical.
*Margins.*—Entire, straight.
*Texture.*—Smooth.
*Color.*—Upper side — 137-A. Under side — 137-C.

THE BUD

Size: Medium.
*Diameter.*—Averaging about 3 mm.
*Length.*—Averaging about 20 mm.
Shape: Cylindrical, long and pointed.
Calyx:
*Shape.*—Cylindrical. The calyx is formed out of 5 pointed sepals of about 5 mm which are joined at the lower point and sharply pointed at the apex.
*Size.*—Averaging 3 mm. in width and 20 mm. in length.
*Splitting.*—The calyx does not split.
*Aspect.*—Smooth.
*Color.*—RHS 137-C.
Flower stem:
*Character.*—Erect.
*Length.*—80–110 cm.
*Color.*—Dark Green.

THE FLOWER

Blooming habit: Intermittent and profuse, from Spring through Fall.
Size of flower: Small.
*Diameter.*—Averaging about 30 mm.
*Depth.*—Averaging about 5 mm.
Borne: In a cluster.
Shape:
*When first opening.*—Flat.
*When mature.*—Flat.
Number of flowers per main flower stem: 25–30.
Petalage:
*Number of petals.*—5.
*Arrangement.*—Side by side around the pistil.
*Form.*—Fan shaped.
*Texture.*—Soft.
*Appearance.*—Velvety.
*Margins.*—Dentate.
*Color.*—When the petals begin to unfurl, the coloration of the petal at the body is RHS 73-A. The body is "mottled" with small spots which have the color of RHS 155-D. The color of the "mottled" portion is 73-D. These spots in the petals are scattered all over the petal body and the number of spots varies from 100–200. The base and the edge of the petals have a color of RHS 155-D. The reverse side has a color of RHS 73-D.
Discoloration after full bloom: Slight.
Persistence: The flowers hang on and dry.
Disease resistance: Resistant to *Fusarium oxysporum,* as observed at Aalsmeer.
Lasting quality: Averaging about 12 days as a cut flower and 21 days on the plant.
Changes with maturity: When the flowers mature, the color of the body turns from RHS 73-A into RHS 73-D. The color of the spots and the base of the petal do not change. The color of the reverse side of the petals is always RHS 73-D.

REPRODUCTIVE ORGANS

Stamens: None.
Anthers: None.
Filaments: None.
Pistils:
*Number.*—1.
Styles:
*Length.*—22 mm. in average.
*Color.*—White.
Stigmas:
*Color.*—White.

FRUIT

Fertility: The fruit is not fertile.
Shape: Pear-shaped.

I claim:

1. A new and distinctive miniature spray carnation plant, substantially as herein shown and described, particularly characterized by its small cyclamen-purple flowers, which are produced profusely in clusters on strong, upright branches of the main stem of a strong, tall, upright bush.

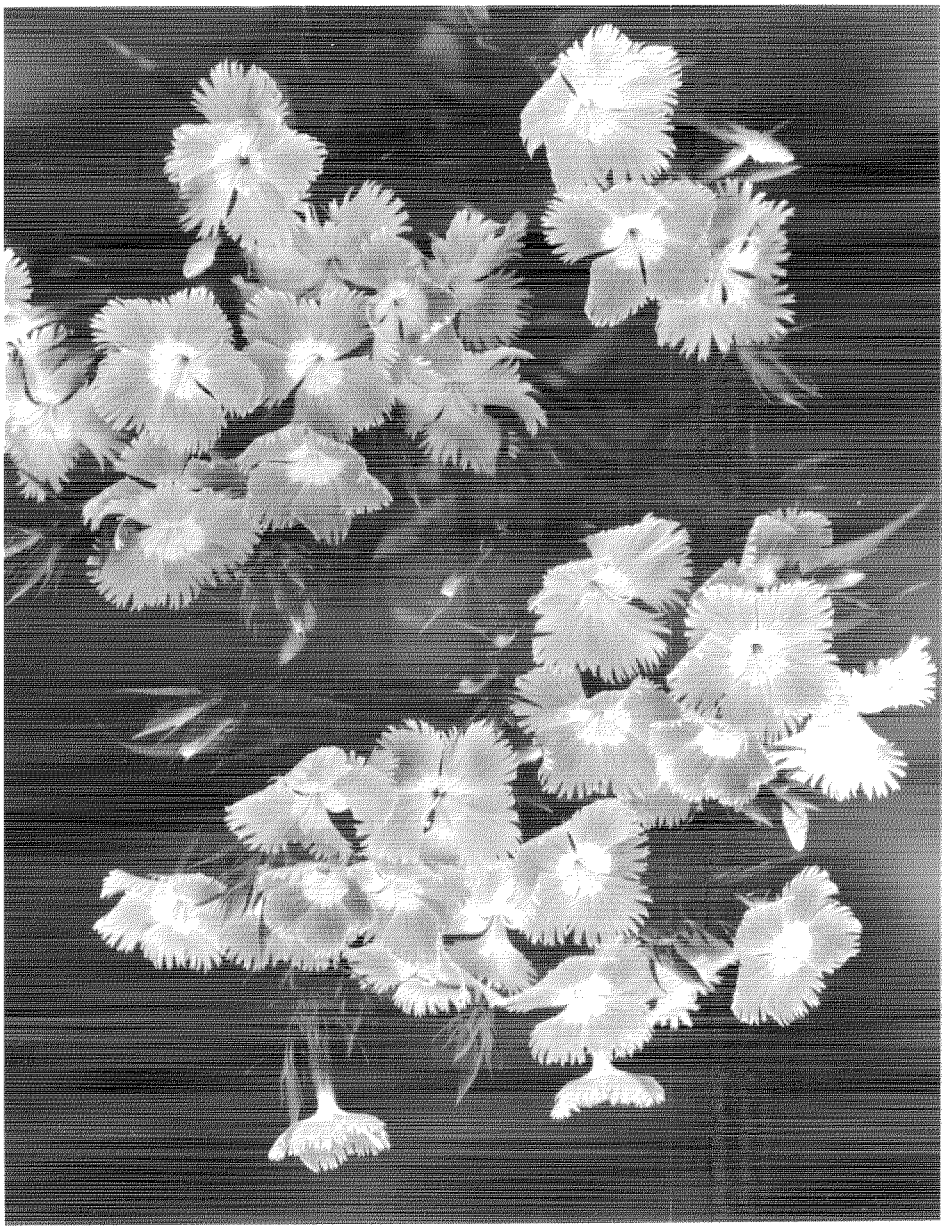

* * * * *